United States Patent [19]

Hinduja et al.

[11] Patent Number: 4,875,363
[45] Date of Patent: Oct. 24, 1989

[54] APPARATUS AND METHOD FOR TESTING FLOW CHARACTERISTICS OF MOLDING COMPOUNDS

[75] Inventors: Murli Hinduja; Mark L. Thompson; John R. Spriggs, all of Fremont, Ohio

[73] Assignee: Sterling Engineered Products Inc., Maumee, Ohio

[21] Appl. No.: 228,373

[22] Filed: Aug. 4, 1988

[51] Int. Cl.⁴ ............................................. G01N 11/04
[52] U.S. Cl. ........................................ 73/56; 73/866; 374/51
[58] Field of Search ............... 73/56, 790, 793, 822, 73/866; 374/51, 53, 55

[56] References Cited

U.S. PATENT DOCUMENTS

| | | | |
|---|---|---|---|
| 1,988,597 | 1/1935 | Jones et al. | 73/806 |
| 2,222,470 | 11/1940 | Barnes | 73/822 |
| 2,259,491 | 10/1941 | Roller | 73/790 |
| 2,302,224 | 11/1942 | Jones | 73/54 |
| 2,574,715 | 11/1951 | Sontag | 73/150 R |
| 2,660,051 | 11/1953 | Dowling | 374/51 |
| 3,033,021 | 5/1962 | Dickason | 374/51 |
| 3,693,458 | 9/1972 | Odell | 73/56 |
| 4,474,066 | 10/1984 | Lutenegger | 73/790 |

Primary Examiner—John Chapman
Assistant Examiner—Michele Simons
Attorney, Agent, or Firm—Marshall & Melhorn

[57] ABSTRACT

An apparatus and method for testing the flow characteristics of molding compounds includes upper and lower mold portions movable relative to one another. The lower mold portion has formed therein a central cavity and a channel extending therefrom with scribe marks formed on a bottom wall of the channel. The upper mold portion has a complimentary raised area for cooperation with the cavity and the channel to force molding compound placed in the cavity to flow down the channel providing an indication of the flow characteristics of the molding compound. Ejector pins positioned in the bottom of the cavity and the channel are actuated by an ejector pin plate which is coupled to the upper mold portion to eject the sample when the mold portions are separated.

17 Claims, 3 Drawing Sheets

APPARATUS AND METHOD FOR TESTING FLOW CHARACTERISTICS OF MOLDING COMPOUNDS

BACKGROUND OF THE INVENTION

The invention relates generally to a testing apparatus and, more particularly, to a tool and method for measuring the flow characteristics of molding compounds.

Among the devices available for testing plasticity and flow characteristics of materials is a plastometer which is disclosed in U.S. Pat. No. 3,033,021. That device includes a mold element having a pair of cavities. A passage leads between the cavities and a plurality of troughs extend radially outwardly from one of the cavities. The troughs are provided for forcing material received within the other one of the cavities through the passage and into the one cavity and the associated troughs. The flow characteristics of the material are measured by the distance of flow of the material in the troughs.

Another prior art device includes a transfer press with an Archimedean spiral mold cut into the fixed platen. However, the mold has a relatively small cross-sectional area. In order to test sheet molding compound with one inch or more glass fiber reinforcing material lengths, the sheet must be cut into smaller pieces which tends to produce inaccurate test results.

SUMMARY OF THE INVENTION

The present invention relates to an apparatus and a method for testing the flow characteristics of molding compounds, especially sheet molding compounds having relatively long reinforcing fibers. An upper mold portion and a lower mold portion are movable relative to one another. The lower mold portion has a central cavity and a channel extending therefrom with scribe marks formed in a bottom wall of the channel. The upper mold portion has a complimentary raised area for cooperation with the cavity and the channel to force molding compound placed in the cavity to flow upon the channel, the scribe marks providing an indication of the flow characteristics. Ejector pins in the lower mold portion are actuated by relative opening movement between the mold portions to remove the tested material from the cavity and the channel.

The width of the channel is selected to provide accurate test results even with sheet molding compound having relatively long reinforcing fibers. Spacer plates are utilized to select the thickness or height of the channel.

It is an object of the present invention to provide a tool and method for testing sheet molding compound having relatively long fibers of glass reinforcing material therein.

BRIEF DESCRIPTION OF THE DRAWINGS

The above, as well as other objects of the invention, will become readily apparent to one skilled in the art from reading the following detailed description of the preferred embodiment of the invention when considered in the light of the accompanying drawings in which.

DESCRIPTION OF THE PREFERRED EMBODIMENT

Figure 1:
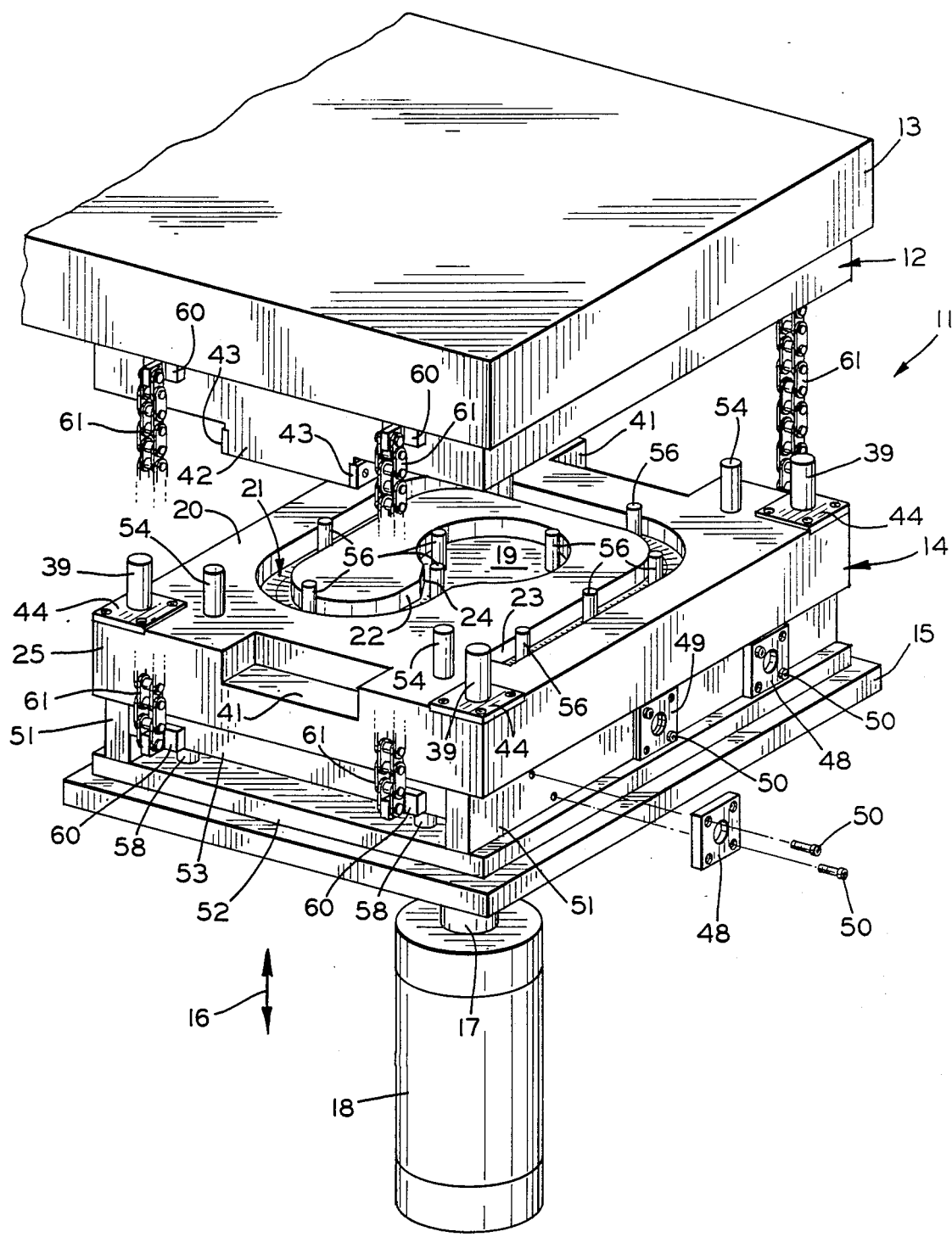
FIG. 1 is a perspective view of a testing apparatus constructed in accordance with the present invention.

As shown in FIG. 1, an apparatus 11 for testing samples of molding compound includes an upper mold portion 12 which is attached to a downwardly facing surface of a generally horizontally extending upper platen 13. A lower mold portion 14 of the apparatus 11 is attached to an upwardly facing surface of a generally horizontally extending lower platen 15.

The upper platen 13 is fixed and the lower platen 15 is movable toward and away from the upper platen 13 as indicated by an arrow 16. The lower platen 15 is mounted on an output shaft 17 of a hydraulic cylinder 18 which raises and lowers the lower platen 15 and the lower mold portion 14. However, the lower platen 15 could be fixed and the upper platen 13 could be movable relative thereto.

Figure 2:
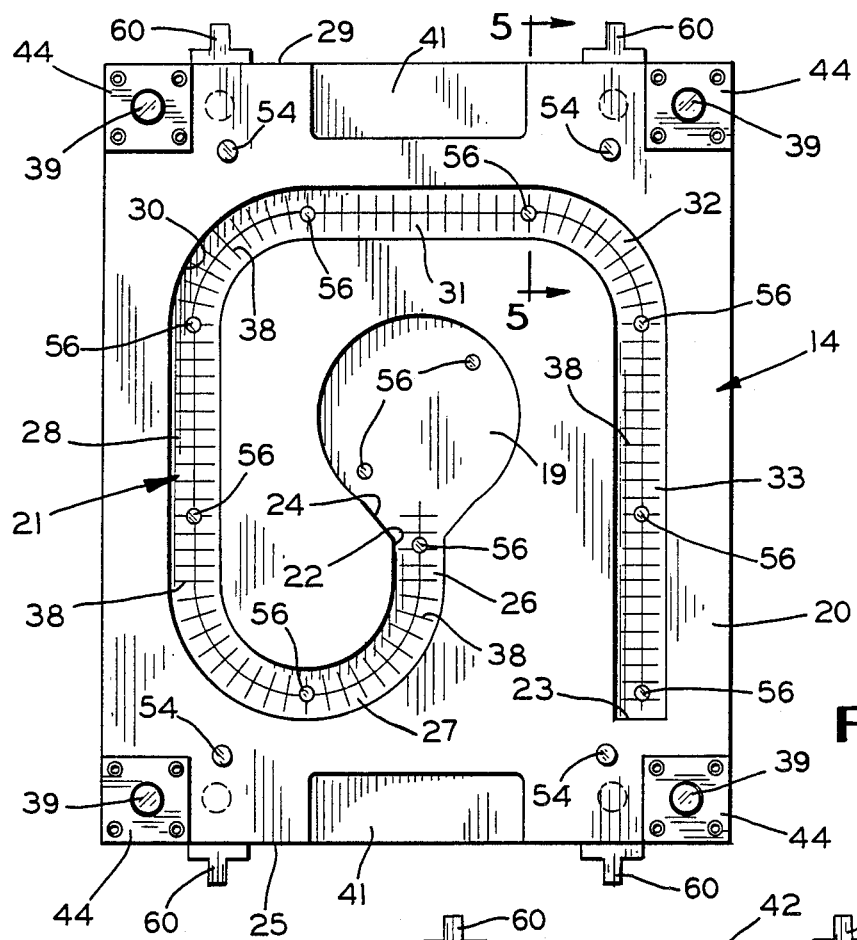
FIG. 2 is a top plan view of the bottom mold portion of the apparatus shown in FIG. 1.

As shown FIGS. 1 and 2, the lower mold portion 14 has a generally circular depression or cavity 19 formed in a central area of its upper surface 20. Also formed in the upper surface 20 is a channel 21 which is connected at one end 22 with the cavity 19 and has an opposite end 23 terminating in a wall of the lower mold portion 14. The channel 21 is of uniform width along its length and the one end 22 widens or flares into a gate area 24 at the connection to the cavity 19.

The channel 21 is formed of a plurality of straight and curved sections. The opening in the wall of the cavity 19 defined by the one end 22 and the gate 24 faces an end wall 25 of the lower mold portion 14. A relatively short straight section 26 extends toward the wall 25 and is connected between the one end 22 and a curved section 27 which defines a one hundred eighty degree change in direction of the channel 21. An opposite end of the curved section 27 is connected to one end of a relatively long straight section 28 which extends toward an opposite end wall 29 of the lower mold portion 14. An opposite end of the straight section 28 is connected to a curved section 30 which extends for approximately ninety degrees before joining a relatively long straight section 31. The straight section 31 extends generally parallel to the end walls 25 and 29. The opposite end of the straight section 31 joins a curved section 32 which extends for approximately ninety degrees before joining a relatively long straight section 33. A straight section 33 extends toward the end wall 25 and terminates in the end 23 of the channel 21.

Figure 3:
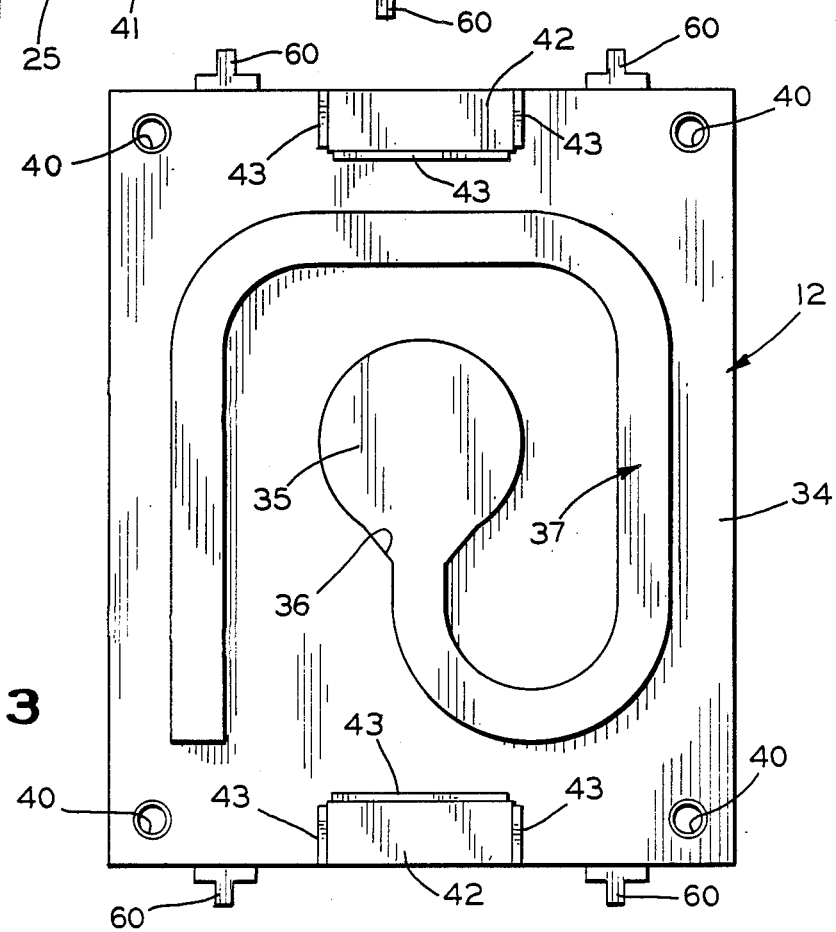
FIG. 3 is a bottom plan view of the top and bottom portion of the apparatus shown in FIG. 1.

As best shown in FIG. 3, there is formed on a lower surface 34 of the upper mold portion 12 a male equivalent of the cavity 19, the gate 24, and the channel 21. A generally circular downwardly extending raised area 35 is connected to a raised gate area 36 which in turn is connected to a raised channel area 37.

In order to test the flow characteristics of molding compound, a sample of a selected molding compound material is placed in the cavity 19. If the material is a sheet molding compound, the sheet must first be broken into pieces of a size which will fit into the cavity 19. The hydraulic cylinder 18 is then actuated to raise the lower mold portion 14 and the lower platen 15 towards the upper mold portion 12 and the upper platen 13. As the raised circular area 35 engages the central cavity 19, pressure is applied to the sample material and the sample begins to flow through the opening defined by the gate areas 24 and 36 and into the channel defined by areas 21 and 37. The distance that the sample material flows down the channel is an indication of the flow characteristics of the sample material. Therefore, a plurality of scribe marks 38 are provided on a bottom wall of the channel 21 to assist in determining the distance the sample material has flowed.

In order to assure that the raised areas 35, 36 and 37 on the upper mold portion 12 properly engage the corresponding depressed areas 19, 24 and 21 in the lower mold portion 14, a guide pin 39 is provided at each corner of the lower mold portion 14. As the lower mold portion 14 approaches the upper mold portion 12, the guide pins 39 engage apertures 40 formed in the four corners of the upper mold portion 12 thereby aligning the raised areas on the upper mold portion 12 with the depressed areas in the lower mold portion 14.

As an additional alignment means, a locator step 41 is formed in each of the end walls 25 and 29 and the upper surface 20 of the lower mold portion 14. A pair of cooperating locator blocks 42 extend downwardly from the lower surface 34 of the upper mold portion 12 for engagement with the locator steps 41. A plurality of shim plates 43 can be attached to the vertically extending surfaces of the locator blocks 42 to engage corresponding vertical walls of the locator steps 41 to precisely position the upper mold portion 12 with respect to the lower mold portion 14.

Figure 4:
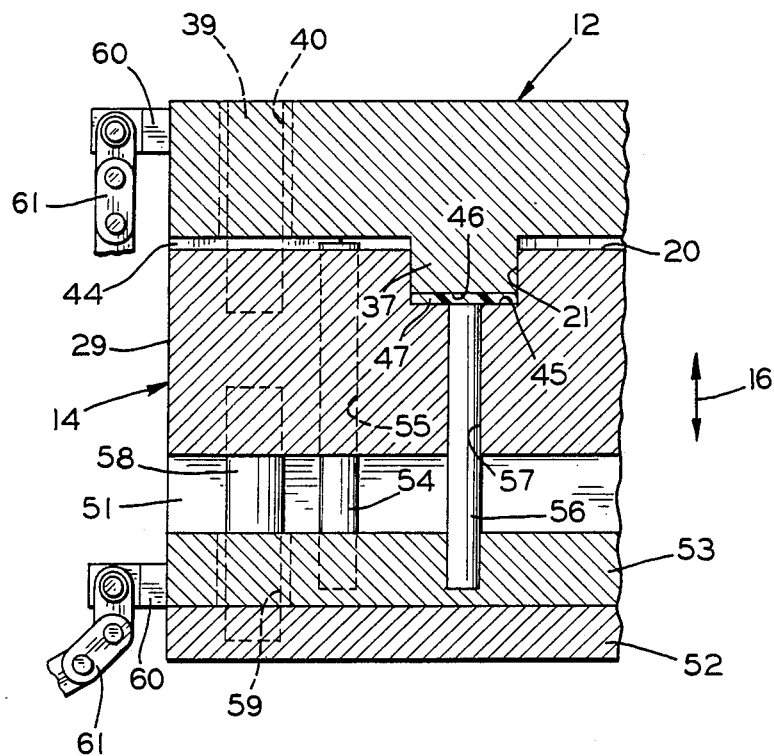
FIG. 4 is an enlarged fragmentary cross-section of the present invention showing the relationship of the top and bottom mold portions just prior to testing a sample of a molding compound.

Referring now to FIGS. 1, 2, and 4, each of the guide pins 39 extends through an associated spacer plate 44 which is attached to the upper surface 20 of the lower mold portion 14. As shown in FIG. 4, the thickness of the spacer plates 44 is selected to determine the spacing between a bottom wall 45 of the channel 21 and an opposed lower surface 46 of the raised channel area 37 on the upper mold portion 12. The distance between the bottom wall 45 and the facing lower wall 46 determines the thickness of a sample 47 of material as it flows through the channel of the test apparatus 11. As shown in FIG. 1, spacing plates of different thicknesses can be conveniently stored by mounting on the testing apparatus 11. For example, a pair of spacer plates 48, which are thicker than the spacer plates 44, and a pair of spacer plates 49, which are thinner than the spacer plates 44, can each be mounted in convenient locations utilizing a pair of fasteners 50. The spacer plates 48 and 49 could be mounted on an outwardly facing surface of one of a pair of beams 51 attached to a lower surface of the lower mold portion 14 and extending between the end walls 25 and 29.

The beams 51 space the lower mold portion 14 above a mounting plate 52 which in turn is attached to the lower platen 15. Positioned between the spacer beams 51 is a generally horizontally extending ejector pin plate 53. Each one of a first plurality of ejector pins 54 has a lower end attached to and extending into an upper surface of the plate 53. The pins 54 extend through apertures 55 formed in the lower mold portion 14. An upper end of each of the pins 54 extends above the upper surface 20 of the lower mold portion 14 a distance which is less than the thickness of the thinnest spacer plates 49. A second plurality of ejector pins 56 also each have a lower end which is attached to and extends into the upper surface of the ejector pin plate 53. The ejector pins 56 extend upwardly through apertures 57 formed in the lower mold portion 14. As shown in FIG. 4, when the mold halves are closed, the upper end of each of the ejector pins 56 is positioned even with the bottom wall 45 of the channel 21. The ejector pins 56 are located in the central cavity 19, the gate area 24, and the channel 21 as shown in FIGS. 1 and 2.

As shown in FIGS. 1 and 4, a second set of guide pins 58 is provided for maintaining a horizontal location of the ejector pin plate 53 as it is raised and lowered. As best shown in FIG. 4, each of the guide pins 58 has a lower end extending into and attached to the mounting plate 52 and an upper end extending into and attached to the lower mold portion 14. Each of the guide pins 58 extends through a corresponding aperture 59 formed in the ejector pin plate 53.

Figure 5:
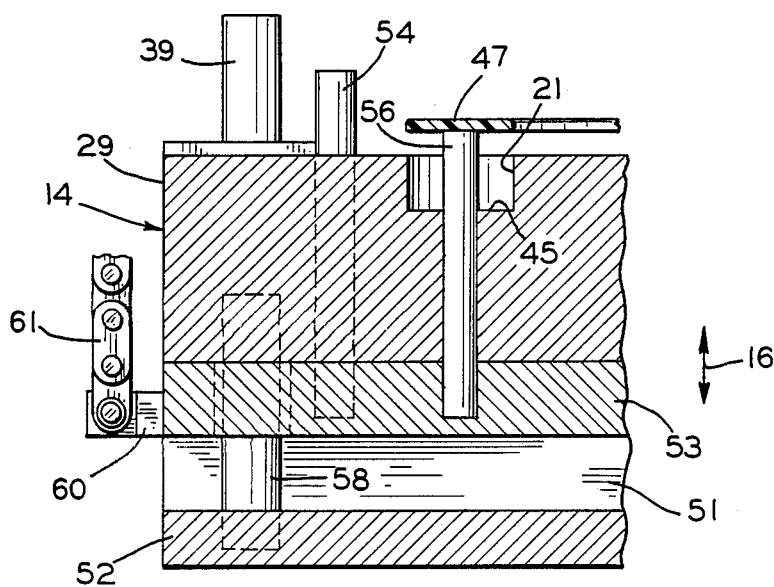
FIG. 5 is an enlarged fragmentary cross-sectional view as if taken along the line 5—5 in FIG. 2 showing the bottom mold portion of the testing apparatus and a sample after testing.

The ejector pin plate 53 is coupled to the upper mold portion 12 for actuating the ejector pins when the lower mold portion 14 is lowered away from the upper mold portion 12. A plurality of lugs 60 are attached to the upper mold portion 12 and the ejector pin plate 53. Connected between associated pairs of the lugs are flexible belts or chains 61. When the upper mold portion 12 and the lower mold portion 14 are in the closed position shown in FIG. 4, the chains 61 are in a relaxed position and the ejector pin plate 53 rests on an upper surface of the mounting plate 52. As the hydraulic cylinder 18 is actuated to lower the lower mold portion 14 away from the upper mold portion 12, the chains 61 begin to straighten and eventually are extended to their full lengths thereby raising the ejector pin plate 53 to the position shown in FIG. 5. In that position, the upper ends of the ejector pins 56 extend above the bottom wall 45 of the channel 21 to force the sample material 47 out of the channel where it can be removed from the lower mold portion 14.

The testing apparatus according to the present invention can be utilized to perform a method of testing the flow characteristics of bulk molding compound or sheet molding compound. In an apparatus constructed according to the preferred embodiment, the cavity 19 was formed with a six inch diameter. The gate area 24 was formed three inches wide at its widest point and one inch long. The channel depression width should be wider than the length of the longest reinforcing fiber. For a one inch fiber length, a one and one half inch channel width was selected. The straight section 26 was formed one and one quarter inches long and the curved section 27 was formed on a two and one half inch radius at its inner wall. The straight section 28 was formed seven and one half inches long and each of the curved sections 30 and 32 was formed with a two and one half inch radius at its inner wall. The straight section 31 was formed five and one quarter inches long while the straight section 33 was formed eleven and one half inches long. The channel 21 was formed one and one half inches wide. The spacer plates 49, 44 and 48 were formed to provide sample thicknesses of 0.080 inches, 0.100 inches and 0.125 inches respectively. The raised areas on the upper old portion 12 are dimensioned to prevent the escape of the molding compound. However, at the end wall 23 clearance is provided for the escape of trapped air as the molds close.

The first step in the method according to the present invention is to separate the upper and lower mold portions 12 and 14. The next step is to select the desired thickness spacer plate and mount the plates on the upper surface 20 of the lower mold portion 14. Next, the molding compound to be tested is placed in the cavity 19 formed in the lower mold portion 14. The hydraulic cylinder 18 is actuated to raise the lower mold portion 14 towards the upper mold portion 12 until the spacer plates engage the lower surface 34 of the upper mold portion 12. The raised circular area 35 formed on the upper mold portion 12 applies pressure to the molding compound in the central cavity 19 causing the molding compound to flow out through the gate 24 and down the channel 21.

When the sample flow is complete, the lower mold portion 14 is lowered away from the upper mold portion 12 thereby exposing the channel 21 and the scribe marks 38. The flow characteristics of the molding compound can be determined by the distance the molding compound flowed down the channel 21. When it is desired to remove the molding compound sample 47 from the lower mold portion 14, the hydraulic cylinder 18 is actuated to remove the slack from the chains 61 thereby raising the ejector pin plate 53 and causing the ejector pins 57 to force the material sample 47 from the central cavity 10, the gate area 24 and the channel 21.

In accordance with the provisions of the present statutes, the present invention has been described in what is considered to represent its preferred embodiment. However, it should be noted that the invention can be practiced otherwise than as specifically illustrated and described without departing from its spirit or scope.

What is claimed is:

1. An apparatus for testing the flow characteristics of molding compounds comprising:
    a first mold portion having a generally circular cavity and a channel depression extending therefrom formed in a surface thereof;
    a second mold portion having a generally circular raised area and a raised channel area extending therefrom formed on a surface thereof, said raised circular and channel areas being complementary to said cavity and channel depression, respectively;
    means for moving said mold portions relative to one another, movement in a direction to separate said surfaces permitting a sample of material to be placed between said surfaces and movement in an opposite direction engaging said circular raised area with said cavity and engaging said raised channel area with said channel depression thereby applying pressure to the sample material causing the sample material to flow in said channel depression;
    a plurality of scribe marks formed in a wall of said channel depression for indicating a flow characteristic of the sample material; and
    means responsive to movement in a direction to separate said surfaces for removing the sample material from said cavity and said channel depression.

2. The apparatus according to claim 1 including spacer means attached to one of said first and second mold portions for engaging the other one of said mold portions to define the distance between a bottom wall of said channel depression and a facing surface of said raised channel area.

3. The apparatus according to claim 2 wherein said spacer means includes spacer plates of a predetermined thickness attached to at least one of said mold portions, said spacer plates being selected from a plurality of spacer plates of different predetermined thicknesses.

4. The apparatus according to claim 3 wherein said plurality of spacer plates include means for releasable attachment to at least one of said mold portions.

5. The apparatus according to claim 1 wherein said means for removing includes a plurality of ejector pins positioned in said circular cavity and in said channel depression and means for actuating said ejector pins for removing the sample material from said circular cavity and from said channel depression.

6. The apparatus according to claim 5 wherein said means for actuating includes an ejector pin plate, said pins being mounted in and extending from said plate, said pins extending through a plurality of apertures formed in said second mold portion, and means coupling said plate to said first mold portion whereby when said mold portions are separated, said pins are extended through said apertures to remove the sample material.

7. The apparatus according to claim 6 wherein said means for coupling includes a plurality of chains connected between said second mold portion and said ejector pin plate.

8. The apparatus according to claim 7 wherein said second mold portion is positioned above said first mold portion and said ejector pin plate is positioned below said first mold portion.

9. The apparatus according to claim 1 including means for guiding said mold portions along a predetermined path defining said direction to separate and said opposite direction.

10. The apparatus according to claim 9 wherein said means for guiding includes a plurality of guide pins attached to and extending from said first mold portion and a corresponding plurality of apertures formed in said second mold portion for accepting said guide pins.

11. The apparatus according to claim 1 wherein said channel depression is formed with a width greater than a longest one of a plurality of reinforcing fibers in the sample material.

12. An apparatus for testing the flow characteristics of molding compounds comprising:
    a lower mold portion having a generally circular cavity and a channel depression extending therefrom formed in an upwardly facing surface;
    an upper mold portion having a generally circular raised area and a raised channel area extending therefrom formed on a downwardly facing surface, said raised circular and channel areas being complementary to said circular cavity and channel depression, respectively;
    means for moving said lower mold portion toward and away from said upper mold portion;
    a plurality of guide pins attached to said lower mold portion and extending through apertures formed in said upper mold portion;
    a plurality of spacer plates of predetermined thickness releasably attached to said upwardly facing surface for engaging said downwardly facing surface and defining a predetermined distance between facing surfaces of said channel depression and said raised channel area; and
    a plurality of scribe marks formed on a wall of said channel depression for indicating a flow characteristic of a sample material.

13. The apparatus according to claim 12 wherein said channel depression and said raised channel area extend from and substantially around said circular cavity and said circular raised area respectively.

14. The apparatus according to claim 12 including an ejector pin plate positioned below said lower mold portion, a plurality of ejector pins attached to said plate, a corresponding plurality of apertures formed in said lower mold portion in said circular cavity and said channel depression, and a plurality of chains connected between said plate and said upper mold portion for extending said ejector pins through said apertures as said means for moving moves said lower mold portion away from said upper mold portion.

15. A method of testing the flow characteristics of a molding compound comprising of the steps of:
 (a) forming a generally circular cavity and a channel depression extending therefrom in a surface of a first mold portion;
 (b) forming a raised generally circular area and a raised channel area extending therefrom on a surface of a second mold portion;
 (c) forming a plurality of spaced apart scribe marks on a wall of said channel depression;
 (d) moving said surfaces apart;
 (e) inserting a sample of a material to be tested between said surfaces;
 (f) moving said surfaces relative to one another to enclose the sample between said cavity and said circular area and to apply pressure to the sample material to cause the material to flow down said channel depression;
 (g) moving said surfaces apart; and
 (h) determining the flow characteristics of the sample material utilizing said scribe marks.

16. The method according to claim 15 wherein said step (c) includes selecting a predetermined distance between opposed surfaces of the channel depression and the raised channel area by providing a plurality of spacer plates on the surface of the first mold portion.

17. The method according to claim 15 including subsequent to step (b) removing the sample material from the cavity and the channel by extending ejector pins through the first mold portion.

* * * * *

UNITED STATES PATENT AND TRADEMARK OFFICE
CERTIFICATE OF CORRECTION

PATENT NO. : 4,875,363
DATED : October 24, 1989
INVENTOR(S) : Murli Hinduja, Mark L. Thompson and John R. Spriggs It is certified that error appears in the above-identified patent and that said Letters Patent is hereby corrected as shown below:

Column 1, line 42, "upon" should read --down--; line 54, --a-- should be inserted after "and".

Column 2, line 1, "and bottom" should be changed to read --mold--.

Column 4, line 63, "old" should read --mold--.

Column 5, line 25, "10" should read --19--; line 26, "present" should read --patent--.

Signed and Sealed this

Fourteenth Day of May, 1991

Attest:

HARRY F. MANBECK, JR.

Attesting Officer

Commissioner of Patents and Trademarks